United States Patent [19]

O'Donnell et al.

[11] 4,260,844
[45] Apr. 7, 1981

[54] NICKEL COMPLEXES IN DIOL SOLVENTS AND THEIR USE AS OLIGOMERIZATION CATALYST PRECURSORS

[75] Inventors: Albert E. O'Donnell; Clarence Gum, both of Houston, Tex.

[73] Assignee: Shell Oil Company, Houston, Tex.

[21] Appl. No.: 116,687

[22] Filed: Jan. 30, 1980

[51] Int. Cl.$^3$ .............................................. C07C 2/02
[52] U.S. Cl. ................................. 585/523; 585/520; 585/525
[58] Field of Search .................... 585/523, 520, 525

[56] References Cited

U.S. PATENT DOCUMENTS

| | | | |
|---|---|---|---|
| 3,644,564 | 2/1972 | Van Zwet et al. | 585/520 |
| 3,647,914 | 3/1972 | Glockner et al. | 585/520 |
| 3,647,915 | 3/1972 | Bauer et al. | 585/523 |
| 3,676,523 | 7/1972 | Mason | 585/523 |
| 3,686,351 | 8/1972 | Mason | 585/523 |
| 3,737,475 | 6/1973 | Mason | 585/523 |
| 3,825,615 | 7/1974 | Lutz | 585/523 |
| 4,020,121 | 4/1977 | Kister et al. | 585/520 |

*Primary Examiner*—Curtis R. Davis
*Attorney, Agent, or Firm*—Al A. Jecminek

[57] ABSTRACT

Ethylene is oligomerized to even numbered alpha-monoolefins principally in the $C_4$ to $C_{40}$ range with minimal concomittant production of high molecular weight polyethylene by reacting ethylene in a diol solvent in an oligomerization reaction zone at elevated pressure with a nickel complex catalyst composition produced by combining in the reaction zone, (a) a stable preformed complex of nickel, ethylene and hydride in a diol solvent, said complex being prepared by contacting in a diol solvent and in the presence of ethylene, a nickel salt, a base and a boron hydride transfer agent and (b) a suitable bidentate ligand; the stable nickel complex solution and the bidentate ligand being added in separate portions to the reaction zone. These stable complexes of nickel, ethylene and hydride in diol solution are considered to be novel oligomerization catalyst precursor compositions.

16 Claims, No Drawings

NICKEL COMPLEXES IN DIOL SOLVENTS AND THEIR USE AS OLIGOMERIZATION CATALYST PRECURSORS

BACKGROUND OF THE INVENTION

This invention relates to a catalyst precursor composition and to an improved process for the production of linear alpha-olefins by catalytic oligomerization of ethylene using a catalyst obtained from the novel precursor composition. More particularly, this invention is directed to a stable complex of nickel, ethylene and hydride in diol solvent and to an ethylene oligomerization process in diol solvent employing a nickel complex catalyst composition formed by adding the pre-formed stable nickel complex in diol solvent and a bidentate ligand in separate portions to the oligomerization reaction zone.

Linear monoolefins are compounds of established utility in a variety of applications. Terminal linear monoolefins, particularly those having 12 to 20 carbon atoms per molecule, are known to be useful as intermediates in the production of various types of detergents e.g. alcohols, ethoxylates, etc.

Several synthetic techniques have been developed for the preparation of terminal linear monoolefins in the detergent range. One very attractive synthetic method from the standpoint of raw material availability and cost involves oliogomerization of ethylene to higher molecular weight linear monoolefins (even numbered alpha-monoolefins) by contact with a catalytically active nickel complex catalysts for ethylene ologomerization is prepared as the reaction product of an olefinic nickel compound, including zero-valent nickel compounds such as bis(cyclooctadiene) nickel (0) or $\pi$-allyl nickel compounds, and a suitable bidentate ligand as described in U.S. Pat. No. 3,644,564 to Van Zwet et al, U.S. Pat. No. 3,647,914 to Glockner et al and U.S. 3,647,915 to Bauer et al. A different and preferred class of nickel complex catalysts can be prepared by contacting in certain polar organic solvents in the presence of ethylene (1) a simple divalent nickel salt which is at least somewhat soluble in the solvent, (2) a boron hydride reducing agent and (3) a suitable bidentate ligand. The preparation of catalysts in this preferred class and their use in ethylene oligomerization are described in U.S. Pat. Nos. 3,676,523, 3,686,351 and 3,737,475 to R. F. Mason and U.S. Pat. No. 3,825,615 to Lutz.

In the above mentioned patents describing ethylene oligomerization with the preferred nickel complex catalysts, it is taught that the catalyst composition is suitably preformed outside the oligomerization reaction zone by mixing together in the presence of ethylene, the various ingredients—i.e., the nickel salt, the bidentate ligand and the boron hydride reducing agent—in the polar organic solvent. This preformed catalytic composition in the polar organic solvent or diluent is then added directly to the reaction zone. In this regard, no real criticality is attached to the order or manner in which the catalyst precursors are combined, in the patent teachings, although it is commonly preferred to contact the solvent, the nickel salt and the bidentate ligand in the presence of ethylene before the boron hydride reducing agent is added to the solution of catalyst precursors.

While the preferred nickel complex catalysts prepared according to the teachings of the aforementioned patents to R. F. Mason and to Lutz provide an attractive means for oligomerizing ethylene to higher linear terminal olefins, in particular those in the detergent range, the resulting oligomerization processes are not devoid of problems. One troublesome aspect of these preferred processes is the propensity of the nickel catalysts to catalyze the formation of objectionable, polymeric polyethylene under certain conditions in the process. This polymeric polyethylene typically has a broad molecular weight range (molecular weight from a few thousand to as high as a few million) in contrast to the desired lower molecular weight oligomer product. As produced in the oligomerization process, such polyethylene is not a usable commercial product and thus only serves to decrease the yield of desired oligomer product from the ethylene feed. Furthermore, it has an even more objectionable effect in that it tends to plug and foul mechanical equipment and transfer lines in the process.

The formation of this polymeric polyethylene in the oligomerization reaction product and its objectionable effect on downstream processing eqiupment is recognized in U.S. Pat. No. 4,020,121 to Kister et al. Specifically, this patent teaches that residual catalyst present in the hydrocarbon (oligomer) phase of the three phase oligomerization reaction product (the other phases being a liquid solvent phase and a gaseous ethylene phase) can promote the formation of polymeric polyethylene when catalyst, solvent and ethylene are present in the hydrocarbon phase at conditions under which part of the hydrocarbon phase is removed by flashing or distillation. According to Kister et al., this polyethylene formation downstream of the oligomerization reaction can be avoided by a stepwise product recovery process in which the hydrocarbon product phase is subject to a scrubbing step using additional liquid reaction solvent prior to the time that the catalyst-contaminated hydrocarbon product phase is subjected to depressurization for removal of ethylene.

A second troublesome source of polymeric polyethylene which is not dealt with in the Kister et al patent is the portion of the oligomerization process which is upstream of the oligomrization reaction itself, that is, the reaction vessel (catalyst maker) used for making the preformed oligomerization catalyst and associated reactant transfer lines into the catalyst maker and out of the catalyst maker to the oligomerization reactor. Here, it is found, particularly when the catalyst preparation is carried out in a continuous fashion using an aliphatic diol reaction solvent, that polymeric polyethylene tends to form and periodically plug off the transfer line from the catalyst maker to the oligomerization reaction zone and the transfer line used to add makeup ethylene to the catalyst maker. Further during periods of minor upset, significant quantities of polymeric polyethylene may form in the catalyst maker itself necessitating shutdown and cleanout operations. When it forms in the catalyst maker, the polymeric polyethylene generally consumes a substantial quantity of the nickel catalyst component present since the resulting product is typically a solid agglomeration of polyethylene and nickel particles.

From the foregoing it can be seen that it would be highly desirable if an alternative means could be devised for preparing and introducing the nickel complex catalyst into the oligomerization reactor which would minimize the formation of undesirable polymeric polyethylene and the equipment plugging and fouling problems associated therewith.

DESCRIPTION OF THE PRIOR ART

In an article entitled "The 'Nickel Effect'" by Fischer et al in Angew. Chem. internat. Edit. Vol. 12, No. 12, December 1973 pp 943-1026 mention is made on pages 951 and 952 of nickel (0) complexes with olefins, specifically tris (ethylene) nickel obtained by treating (cyclododecatriene) nickel with ethylene at 0° C. However, this tric (ethylene)-nickel complex is characterized as being rather unstable ("extremely sensitive") and there is no indication in the article that the nickel olefin complexes could have practical value as precursors for nickel complex oligomerization catalysts.

SUMMARY OF THE INVENTION

A simple and economic technique has now been found to minimize polymeric polyethylene formation in ethylene oligomerization reaction systems employing aliphatic diol reaction solvents containing nickel complex catalysts prepared by combining, in the presence of ethylene, a simple divalent nickel salt, a boron hydride transfer agent, a base and a suitable bidentate ligand. In this improved process, ethylene is oligomerized to even numbered alpha-monoolefins by reacting ethylene in a diol solvent in an oligomerization reaction zone at elevated pressure with a nickel complex catalyst composition produced by combining in the reaction zone (a) a stable preformed complex of nickel, ethylene and boron hydride in a diol solvent, said complex being prepared by contacting in a diol solvent and in the presence of ethylene, (1) a simple divalent nickel salt, (2) a base and (3) a boron hydride transfer agent and (b) a suitable bidentate ligand; the stable preformed complex of nickel in diol solvent and the bidentate ligand being added in separate portions to the reaction zone. By performing the stable complex of nickel, ethylene and hydride in diol solvent and adding it to the oligomerization reaction zone separately from the bidentate ligand, it has been found not only that the problem of polymeric polyethylene formation which plagued the catalyst preparation phases of the prior art oligomerization processes, discussed above, have been solved but, additionally and quite surprisingly, the catalyst utilization in the reaction zone is also enhanced since oligomer product can be produced at a rate equivalent to the prior art processes with a significant reduction in the consumption of nickel salt and boron hydride. This reduced consumption of nickel salt and boron hydride reducing agent has a further benefit in that there is less tendency for fouling when the diol solvent is recovered from the reaction product using a recovery system such as that described in U.S. Pat. No. 4,020,121 to Kister et al.

Accordingly, the present invention provides an improved process for the oligomerization of ethylene to linear alpha olefins which comprises reacting ethylene in a diol solvent in an oligomerization reaction zone at elevated pressure with a nickel complex catalyst composition produced by combining in the reaction zone (a) a stable preformed complex of nickel, ethylene and hydride in a diol solvent, said complex being prepared by contacting in the diol solvent and in the presence of ethylene (1) a simple divalent nickel salt (2) a base and (3) a boron hydride transfer agent and (b) a suitable bidentate ligand; the stable nickel complex in diol solvent and the bidentate ligand being added in separate portions to the reaction zone. Also within the scope of the present invention is the stable preformed complex solution of nickel, ethylene and hydride in diol solvent which functions as a catalyst precursor for the nickel complex catalyst composition employed in the oligomerization process of the invention.

DESCRIPTION OF THE PREFERRED EMBODIMENTS

The improved process of the invention and the novel nickel complex catalyst precursor solutions employed therein are broadly applicable to any ethylene oligomerization process employing a diol reaction solvent and a nickel complex catalyst derived from combining a simple divalent nickel salt, a boron hydride reducing agent and bidentate ligand in the presence of ethylene and the diol solvent. In particular the improvement according to the invention is suitably employed in ethylene oligomerization processes utilizing an organophosphine bidentate ligand such as those described in U.S. Pat. Nos. 3,676,523, 3,686,351 and 3,737,475 all to R. F. Mason and U.S. Pat. No. 3,825,615 to Lutz. As is taught in these patent disclosures, which are herewith incorporated by reference, the bidentate chelating ligand is suitably an organophosphorine having a tertiary organophosphorus moiety with a suitable functional group substituted on a carbon atom attached more than two carbon atoms from the phosphorus atom of the organophosphorus moiety. Representative ligands of this type are compounds of the general formula:

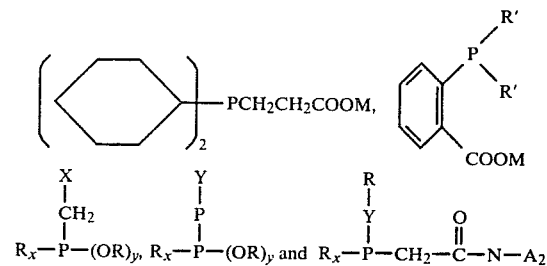

wherein R, independently, is a monovalent organo group, R' a monovalent hydrocarbyl group, X is carboxymethyl or carboxyethyl; Y is hydroxymethyl, mercaptomethyl, hydrocarbyl of up to 10 carbon atoms or hydrycarbyloxy carbonyl of up to 10 carbon atoms; A is hydrogen or an aromatic group of up to 10 carbon atoms; M is hydrogen or an alkali metal, preferably sodium or potassium; x and y are zero, one or two and the sum of x and y is two, with the proviso that when x is two the R groups may together with the phosphorus atom form a mono- or bicyclic heterocyclic phosphine having from 5 to 7 carbon atoms in each ring thereof. Preferred ligands are o-dihydrocarbylphosphinobenzoic acid or its alkali metal salt as described in U.S. Pat. No. 3,676,523 with o-diphenylphosphinobenzoic acid being most preferred. Another preferred ligand, described in U.S. Pat. No. 3,825,615, is dicyclohexylphosphinopropionic acid or its alkali metal salt.

The nickel salt employed to make up the stable nickel complex catalyst precursor and the oligomerization catalyst is suitably any simple divalent nickel salt which is sufficiently soluble in the diol solvent to provide a catalytically effective concentration of nickel complex catalyst. By the terms "simple divalent" nickel salt is meant a nickel atom having a formal valence of +2 and bonded through ionic or electrovalent linkages to two singly charged anionic groups (e.g., halides) or to one doubly charged anionic group (e.g., carbonate) and not complexed with or coordinated to any other additional molecular or ionic species with the exception of waters of hydration. Simple divalent nickel salts therefore do not encompass complex divalent nickel salts which are bonded to one or two anionic groups and additionally complexed or coordinated to neutral chelating ligands or groups such as carbon monoxide and phosphines. However, simple divalent nickel salts are meant to include nickel salts containing water of hydration in addition to one or two anionic groups. Suitably, the simple divalent nickel salt employed to prepare the catalyst precursor and oligomerization catalyst will have a solubility of at least 0.0005 mole per liter (0.0005 M) in the diol solvsent. A solubility in the diol solvent used to prepare the nickel catalyst precursor is preferably at least 0.001 mole of nickel salt per liter (0.001 M) and most preferably at least 0.005 mole of nickel salt per liter of diol solvent (0.005 M). In this regard suitable divalent nickel salts include inorganic nickel salts as well as organic divalent nickel salts. Illustrative inorganic nickel salts are nickel halides such as nickel chloride, nickel bromide and nickel iodide, nickel carbonate, nickel chlorate, and nickel nitrate. Illustrative organic divalent nickel salts are nickel salts of carboxylic acids such as nickel alkanoates of up to 10 carbon atoms, preferably of up to 6 carbon atoms, e.g., nickel formate, nickel acetate, nickel propionate, nickel hexanoate and the like; nickel oxalate, nickel benzoate and nickel naphthenate. Other suitable organic salts include nickel benzenesulfonate, nickel citrate, nickel dimethylglyoxime and nickel acetylacetonate. Nickel halides, especially nickel chloride, and nickel alkanoates, especially nickel acetate, in part because of their availability at low cost and solubility in diol solvents, are preferred nickel salts.

As a general matter, any boron hydride salt reducing agent of reasonable purity can be suitably employed to prepare the stable nickle complex catalyst precursor of the invention. Specific examples include alkali metal borohydrides such as sodium borohydrides, potassium borohydride and lithium borohydride; alkali metal alkoxyborohydrides wherein each alkoxy has 1-4 carbon atoms, such as sodium trimethoxyborohydride and potassium tripropoxyborohydride and tetraalkylammonium borohydrides wherein each alkyl has 1-4 carbon atoms, such as tetraethylammonium borohydride. Largely because of commercial availability, alkali metal borohydrides are preferred and especially preferred is sodium borohydride.

The diol solvent used both to prepare the stable nickel complex catalyst precursor of the invention and as the reaction solvent in the improved oligomerizations process of the invention is an aliphatic diol of 2 to 7 carbon atoms. While different aliphatic diol solvents may be employed in the preparation of the catalyst precursor and in the oligomerization reaction itself, it is preferable to use the same diol solvent in both operations. In this regard, suitable aliphatic diols include vicinal alkane diols such as ethylene glycol, propylene glycol, 2-methyl-1,2-propane-diol, 1,2-butanediol and 2,3-butanediol and alpha-omega alkane diols such as 1,4-butanediol, 1,5-pentanediol, 1,6-hexanediol and 1,7-heptandiol. Alpha-omega alkane diols of 4 to 6 carbon atoms are preferred solvents with 1,4-butanediol being particularly preferred. In some cases it may be desirable to employ mixtures of the abovementioned alkane diols as the solvent source for the catalyst precursor preparation and/or the oligomerization reaction.

The base employed in combination with the nickel salt, the boron hydride transfser agent and ethylene to make up the stable nickel complex catalyst precursor in diol solvent is suitably an alkali metal or alkaline earth metal hydroxide. In this regard it is preferable to employ alkali metal hydroxides with sodium or potassium hydroxide being most preferred. Typically, the base is used aes about a 0.1 to 3.0 M solution in water.

To effect the improvement according to the invention, the stable nickel complex catalyst precursor in diol solvent is prepared in a reaction zone apart from the oligomerization reaction zone and then added separately to the reaction zone along with the desired bidentate ligand. This catalyst precursor preparation step may be carried out batchwise or continuously and is suitably accomplished by contacting or mixing together in the aliphatic diol solvent and in the presence of ethylene the nickel salt, the boron hydride reducing agent and the base. The order in which the nickel component, boron hydride component and base are combined in the presence of ethylene and the diol solvent in the reaction zone is important. For best results, the nickel salt in diol solution and the base in aqueous solution are added to the diol solvent and to this mixture, the aqueous boron hydride containing some base as a stabilizing agent is added. As noted above, it is essential that the nickel complex catalyst precursor be prepared in the presence of ethylene. Suitably, the ethylene pressure and contacting conditions should be sufficient to saturate the catalyst precursor solution with ethylene. Typically, the ethylene pressures employed may be in the range of from 10 to 5000 psig or higher with pressures in the range of from about 500 to about 2000 psig being preferred. The molar ratio of nickel to boron hydride reducing agent in the preparation of the catalyst precursor suitably ranges from about 0.2:1.0 to about 2.0:1.0 with molar ratios of about 0.5:1.0 to 1.0:1.0 being preferred. Similarly, the molar ratio of nickel to the base component is suitably in the range of about 0.33:1.0 to about 10.0:1.0 with ratios of about 0.5:1.0 to 40:1.0 being preferred. In preparing the catalyst precursor sufficient diol solvent is used to provide a nickel complex solution containing from about 0.0002 to 0.2% by weight nickel. This diol solvent may be added together with the nickel salt as a diol solution of the nickel salt or alternatively, all or a portion of the diol solvent may be added as a separate charge to the catalyst precursor preparation reaction zone.

The reaction temperatures required to prepare the stable nickel complex in diol solvent in the catalyst precursor preparation reaction zone suitably range between about 0° and about 100° C. with temperatures in the range of 20° to 50° C. being preferred. In any case, reaction temperatures above about 100° C. should be avoided to minimize decomposition of the nickel complex catalyst precursor and if the resulting diol solution of nickel complex catalyst precursor is to be stored prior to use in the oligomerization reaction, its temperature should be maintained below about 40° C. to insurance optimum stability. The reaction time required to complete the catalyst precursor complex formation typically is less than one minute. Upon completion of the nickel complex forming reaction in the diol solvent, it is essential to the stability of the nickel complex that the solvent containing the nickel complex catalyst precursor be maintained under sufficient ethylene pressure to insure solution saturation with ethylene during transport and storage of the catalyst precursor solution.

In a preferred aspect of the invention, the nickel complex catalyst precursor solution in diol solvent is prepared continuously by charging the boron hydride reducing agent e.g., sodium borohydride, and the base e.g., potassium hydroxide, as a premixed aqueous solution to an agitated reaction vessel maintained at under ethylene °C. pressure e.g., 1500 psig, simultaneous with the addition of a solution of the simple divalent nickel salt e.g., nickel chloride, in the aliphatic diol solvent e.g., 1,4-butanediol. In this preferred embodiment, the flow rates of the mixed aqueous stream containing boron hydride and base and the aliphatic diol stream containing nickel salt are controlled to afford a nickel to boron hydride molar ratio of about 0.6:1.0 and a nickel to base molar ratio of about 2.0:1.0. If desired, all of the aliphatic diol solvent can be added with the nickel salt or alternatively a portion of the diol solvent recovered from the oligomerization reaction in accordance with the process of U.S. Pat. No. 4,020,121 may be added as a separate stream to afford the desired concentration of nickel complex catalyst precursor in the diol solvent. For this preferred embodiment, sufficient diol solvent is added on a continuous basis to give a nickel complex concentration, based on nickel, in the diol solvent of about 0.015% by weight. Further, the reaction vessel size and the flow rates of reactants are selected to give the reactants at least a 1 minute residence time in the reaction vessel prior to withdrawal and changing to the oligomerization reaction zone.

The structure of the nickel complex catalyst precursor in diol solvent prepared as indicated above has not been determined. Based on known behavior of nickel with cyclooctadiene and other olefins, it is possible that the structure is a complex in which two molecules of ethylene are combined with one molecule of chemically reduced nickel (nickel bonded to at least one hydrogen atom). When formed from nickel chloride, potassium hydroxide, sodium borohydride and ethylene, a 1,4-butane diol solution of this nickel complex has the following properties: (a) it is a clear colorless solution, (b) it is only stable under ethylene pressure—when depressured it darkens rapidly with deposition of nickel metal, (c) it reduces aqueous iodine solution, (d) it is decomposed at acidic pH and (e) in aliphatic diol/hydrocarbon systems, it distributes strongly in favor of the aliphatic diol. As indicated previously, the nickel complex catalyst precursor solutions of the invention are relatively stable and, even at temperatures of 80°–90° C., the half life of the catalyst precursor complex is sufficient (about 10 minutes) that when combined with an appropriate bidentate ligand the rate of formation of oligomerization catalyst at these temperatures clearly exceeds the rate catalyst precursor decomposition. This finding of catalyst precursor stability is critical to the operability of the process of the invention because the oligomerization reaction is typically carried out at such elevated temperatures.

In the improved process of the invention, ethylene is oligomerized by reacting ethylene in an aliphatic diol solvent, in an oligomerization reaction zone at elevated pressure with a nickel complex catalyst formed by combining in the reaction zone (a) an aliphatic diol solution of a nickel complex catalyst precursor prepared as described above and (b) a suitable bidentate ligand; the nickel complex catalyst precursor solution and the bidentate ligand being added in separate portions to the reaction zone. The reaction temperatures employed to oligomerize ethylene with the improvement according to the invention suitably range between about 50° and about 150° C. with temperatures in the range of from about 80° to 120° C. being preferred. The pressure in the oligomerization reaction zone must be at least sufficient to maintain the reaction mixture substantially in the liquid phase although excess ethylene will be present in the vapor phase. In this regard, total reaction zone pressures of from about 300 to 5000 psig are suitably employed. Of greater importance to the operability of the oligomerization process is the partial pressure of ethylene in the reaction zone since ethylene partial pressure is a primary factor in maintaining the desired ethylene concentration in the diol solvent phase where the oligomerization reaction takes place. Satisfactory reaction rates can be obtained in the oligomerization process of the inventions with ethylene partial pressures in the reaction zone of from about 400 to 2500 psig. Preferably, the ethylene partial pressure in the reaction zone is maintained at between about 1000 and 2500 psig. The improved oligomerization catalyst employed in the process of the invention is formed in the oligomerization reaction zone by adding the diol solution of nickel complex catalyst precursor and bidentate ligand in a molar ratio of catalyst precursor (based on nickel) to bidentate ligand of from about 0.5:1.0 to about 5.0:1.0, with preferred ratios being in the range of about 1.0:1.0 to 2.5:1.0. When its preferred phosphine ligands of U.S. Pat. No. 3,676,523 to Mason and U.S. Pat. No. 3,825,615 to Lutz i.e., o-diphenylphosphinobenzoic acid and dicyclohexylphosphinopropionic acid are employed, exceptional catalyst activity is obtained with nickel complex catalyst precursor to phosphine ligand molar ratios of about 1.5:1.0. In contrast, with the preformed nickel-ligand catalyst systems of the prior art, such as the catalysts disclosed in the aforementioned U.S. patents, it is necessary to maintain the molar ratio of nickel to ligand in the range of about 2.0:1.0 to obtain similar oligomerization catalyst activity. This reduced consumption of nickel and boron hydride reducing agent obtained with the present process provides a clear advantage for the present invention over the prior art both from the standpoint of catalyst cost and ease of product recovery. With the oligomerization process of the invention, the nickel complex catalyst precursor and bidentate ligand are added to the reaction zone to provide a concentration of catalyst (calculated as parts per million of ligand in the diol reaction solvent) of at least 10 ppm, with catalyst concentrations of from about 50 to about 1000 ppm being preferred and concentrations of from 75 to 125 ppm being most preferred. In this regard, the amount of aliphatic diol reaction solvent present in the reaction zone may suitably range up to 30 liters per mole of ethylene with from about 0.1 to 1.0 liters of solvent per mole of ethylene being preferred.

The improved oligomerization process of the invention may be carried out in batch or continuous manner. In a suitable batch operation the reactant ethylene and catalyst components i.e., nickel complex catalyst precursor in diol solvent and bidentate ligand, are added as separate components to an agitated reaction vessel, with the ethylene partial pressure in the vessel being maintained at a preselected pressure throughout the reaction period i.e. 10 to 1000 minutes. Since ethylene is consumed during the oligomerization reaction, additional ethylene is added on an incremental basis during the batch reaction to maintain the desired ethylene partial pressure. Further, if desired, part of the diol reaction solvent may be added as a separate component to the reaction vessel. As ethylene is oligomerized during the course of the batch reaction, a separate hydrocarbon or oligomer liquid phase forms in the reaction vessel such that the reaction product consists of a three phase mixture i.e., an ethylene vapor phase, a liquid diol solvent phae containing dissolved catalyst and a liquid hydrocarbon or oligomer product phase containing dissolved ethylene, as well as small amounts of diol solvent and catalyst.

Preferably, the improved oligomerization process of the invention is carried out in a continuous fashion. With certain modifications, this preferred mode of conducting the process of the invention may be carried out using the reaction system described in U.S. Pat. No. 4,020,121 to Kister et al.; the modifications being the use of the catalyst preparation zone to make the stable nickel complex catalyst precursor solution in diol solvent and the separate addition of this catalyst precursor solution and the bidentate ligand to the reaction loop. In particular, a preferred reaction system for continuous oligomerization of ethylene in accordance with the invention includes two or more (most preferably three) time tank reactors arranged in series with appropriate pumping for continuous circulation of the reaction mixture through the reactors. Each time tank reactor is followed by a heat exchanger through one side of which a heat exchange fluid is circulated to remove heat of reaction and thus to maintain the appropriate temperatures in the reactors. The inlet lines for the two components making up the catalyst i.e., the nickel complex catalyst precursor in diol solution and the bidentate ligand, are separated so that the nickel complex catalyst precursor solution and the bidentate ligand are added into the reaction loop upstream of two different reaction stages. Preferably, the bidentate ligand is added to the circulating reaction mixture at a point upstream of the point at which the nickel complex solution is added. For example, in the three stage reaction system the bidentate ligand is added from storage through an inlet port located immediately upstream of the first or second time tank reactor stage whereas the diol solution of nickel complex catalyst precursor is made as described above in a continuous catalyst precursor prepartion vessel and added to the circulating reaction mixture in the oligomerization reaction loop immediately upstream of the second or third reaction stage, respectively. The complete reaction requirement of ethylene may be added continuously along with the diol solution of nickel complex catalyst precursor i.e., via ethylene charge to the catalyst precursor preparation vessel, or a portion of the ethylene may be added as a separate stream to the reaction loop. Preferably, only a small fraction of the ethylene feed is added at catalyst precursor preparation vessel (to maintain precursor stability), and most of the ethylene is added separately to the oligomerization reaction loop. Similarly, all of the aliphatic diol reaction solvent may be added with the nickel complex catalyst precursor or a portion of the solvent may be added as a separate stream to the reaction loop. The time tank reactors and reaction loop are sized and the flows of catalyst components are controlled to give the circulating reaction mixture a sufficient residence time e.g., 5 to 50 minutes, based on reactor volume and liquid circulation rate, so that a portion of the finished oligomer product can be withdrawn from the circulating reaction mixture leaving the third reaction stage and passed to product recovery. Typically the portion of the reaction mixture split off and sent to product recovery will be no more than 10%w of the total circulating reaction mixture in the reaction loop. This reaction product is also comprised of the three phases mentioned above for the batch reaction process.

Regardless of whether the oligomerization is carried out batchwise or continuously, the oligomer product, diol solvent, active catalyst and unreacted ethylene are suitably recovered from the reaction loop effluent using the recovery technique disclosed in U.S. Pat. No. 4,020,121 to Kister et al as modified by the aqueous acid hydrolysis and extraction procedure described in U.S. Pat. application Ser. No. 50,904 filed June 21, 1979 (common assignee). The disclosures of the aforementioned U.S. Pat. application and U.S. Pat. No. 4,020,121 are herewith incorporated by reference for their teaching of a preferred product recovery process. In summary terms, the combined teachings of these two references provide for a stepwise product and solvent recovery scheme wherein (a) the reaction effluent is fed to a gas liquid separation zone wherein gaseous ethylene is separated from the liquid product at temperatures and pressures approximating the reaction zone conditions; (b) the separated liquid product comprising the liquid solvent phase and hydrocarbon phase is passed to one or more liquid-liquid separation zones in which a substantial portion of liquid diol solvent and catalyst complex are removed to afford a liquid hydrocarbon product phase containing dissolved ethylene and a small amount of solvent and catalyst complex; (c) the phase separated liquid hydrocarbon product is scrubbed with purified or fresh diol reaction solvent under sufficient pressure to avoid flashing of dissolved ethylene, said solvent serving to remove residual active catalyst from the hydrocarbon phase; (d) the catalyst-free, hydrocarbon product is passed to a deethenizer wherein dissolved ethylene is flashed off at reduced pressure to afford a deethenized ydrocarbon product containing minor amounts of diol solvent; (e) the deethenized product is washed with water to remove residual diol solvent thereby affording a liquid oligomer product essentially free of solvent, catalyst and ethylene; and (f) the water washed liquid oligomer product is contacted with sufficient aqueous acid (pH below about 5) at elevated temperatures to hydrolyze and extract any diol solvent decomposition products which form during oligomerization and/or aforementioned recovery steps. Applying this recovery process to the improved oligomerization process of the invention, the gaseous and entrained ethylene recovered in steps (a) and (d) is suitably passed back to the catalyst precursor preparation vessel and/or the reaction loop and the diol solvent containing active catalyst recovered in steps (b) and (c) is suitably recycled to the catalyst precursor preparation vessel and/or directly to the reaction loop. The purified oligomer product obtained using this recovery technique is suitably passed to a product work-up system typically consisting of a series of fractionation columns for recovery of the various oligomer fractions. The alpha olefins products may be recovered as individual carbon number alpha olefins, e.g., $C_{10}$, $C_{12}$, $C_{14}$, etc., or as mixtures of even carbon numbers.

The effectiveness of the improved oligomerization process of the invention is demonstrated by the following illustrative embodiments.

ILLUSTRATIVE EMBODIMENT I

The stability of the nickel complex catalyst precursor in an aliphatic diol solution ws demonstrated by heating representative samples of 1,4-butanediol solutions of a nickel complex catalyst precursor for extended periods of time under ethylene pressure and analyzing intermittantly for loss of nickel complex. The 1,4-butanediol solutions of the nickel complex catalyst precursor were prepared by combining 2.6 to 11.9 millimoles of nickel chloride hexahydrate ($NiCl_2.6H_2O$), 1000 g of 1,4-butanediol, 3.4 to 15.5 millimoles of sodium borohydride and 1.14 to 5.2 millimoles of portassium hydroxide in a 4 liter Magnadrive autoclave maintained under an ethylene pressure of 700 psig at 25° C. After additions of the catalyst precursor components to the autoclave, the 1,4-butandiol solution was agitated under ethylene pressure at 24° C. for a period of time and then heated slowly to about 87° C. (typical oligomerization) reaction temperature) with a corresponding increase in the ethylene partial pressure. To determine the stability of the nickel complex catalyst precursor solution at various temperatures, samples of the solution were periodically withdrawn and tested for total reducing power by iodimetry.

The total reducing power (TRP) of samples of catalyst precursor in diol was measured as follows: A weighed sample of catalyst precursor solution was taken into a known amount of aqueous tri-iodide solution under an inert atmosphere. Some of the iodine was reduced by the catalyst precursor. The remaining iodine was measured by titration with standard sodium thiosulfate solution. The total reducing power was calculated as the difference between this titration and the titration of a blank which contained iodine solution but no sample.

Experimental data suggest that one equivalent of reducing power is measured for each mole of nickel which is present in the diol solution as catalyst precursor. Because of residual borohydride decomposition which occurs in the first 15–20 minutes of the tests the base level for determining actual stability of the nickel complex was taken from the sample withdrawn at 30 minutes after the catalyst precursor components had been combined. The results of the stability tests including relevant test conditions are given below in Table I.

TABLE I

| Catalyst Precursor Solution | | | Ethylene Pressure (psig) | Temperature °C. | Half life (min.) |
|---|---|---|---|---|---|
| Ni conc (μm/g) | KOH:Ni Mole Ratio | $NaBH_4$:Nickel Mole Ratio | | | |
| 11.9 | 0.44:1 | 1.3:1 | 700 | 25 | >250 |
| 11.9 | 0.44:1 | 1.3:1 | 1300 | 87 | 22 |
| 2.63 | 0.44:1 | 1.3:1 | 700 | 25 | >300 |
| 2.63 | 0.44:1 | 1.3:1 | 1300 | 87 | 15 |

ILLUSTRATIVE EMBODIMENT II

To demonstrate the improved process of the invention, ethylene was oligomerized in a continuous reaction system using a preformed nickel-ligand complex catalyst prepared according to the prior art in the first part of the test followed by ethylene oligomerization with a catalyst composition made using the same catalyst components but prepared according to the invention by adding the diol solution of nickel complex catalyst precursor and ligand to the oligomerization reaction zone as separate streams. The reaction system employed for this test program included an agitated vessel which served as the catalyst preparation vessel for the preformed catalyst case and as the catalyst precursor preparation vessel in the improvement according to the invention. The oligomerization reaction was carried out in both cases in a reaction loop comprised of three time tank reactors arranged in series with a pump and recycle line for continuous circulation of the reaction mixture through the reactors, and with reactor intercoolers for control of temperature. In both cases, the excess ethylene, oligomer product, solvent and catalyst were recovered using the process described in U.S. Pat. No. 4,020,121 to Kister et al. In part of the test run carried out according to the prior art, the catalyst was prepared by combining the nickel salt component and the ligand component, both in diol solvent, in a line leading to the catalyst preparation vessel whereas the boron hydride component and base component were separately added to the catalyst preparation vessel as a premixed aqueous solution. Ethylene required for the preformed catalyst was added to the catalyst preparation vessel via a separate line along with additional diol solvent. All of the oligomerization reaction requirement of diol solvent was added to the reaction system via the catalyst preparation vessel, but the bulk of the ethylene was added directly to the reactor loop. After start up, the fresh diol solvent added directly to the catalyst preparation vessel was replaced with diol solvent recovered from the oligomerization reaction product. Further, part of the ethylene recovered from the reaction product was also recycled to the catalyst preparation vessel after start up of the oligomerization reaction, and the rest of the recycle ethylene was added directly to the reactor loop. In the oligomerization using the preformed nickel complex catalyst of the prior art, the catalyst in diol solution and its contained ethylene were added to the oligomerization reaction loop at a point immediately upstream of the third reactor stage. For the improvement according the invention, the oligomerization reaction system was modified so that the ligand component was added in diol solution as a separate stream to the oligomerization reaction loop; the point of addition being immediately upstream of the second reactor stage. Thus, in the improvement according to the invention, the catalyst preparation vessel was used only to make the nickel complex catalyst precursor by combining the simple nickel salt, the boron hydride reducing agent and the base in the presence of ethylene and diol solvent in the manner described above for making the preformed catalyst; the only difference being that the ligand component was diverted directly to the reaction zone. As in the case of the preformed catalyst, the nickel complex catalyst precursor solution was added to the oligomerization reaction loop at a point upstream of the third reactor stage. In both cases, oligomerization reaction product was withdrawn from the reactor loop at a point downstream from the third reactor stage. This product was made up of a liquid solvent phase containing nickel complex catalyst and saturated with ethylene, a liquid hydrocarbon or oligomer phase dispersed in the solvent phase and containing dissolved ethylene, solvent and catalyst, and a gaseous ethylene phase.

The test program (both phases) was carried out using 1,4-butanediol as the catalyst preparation and oligomerization solvent, nickel chloride hexahydrate ($NiCl_2.6H_2O$) as the nickel salt catalyst component, sodium borohydride as the boron hydride catalyst component, potassium hydroxide as the base catalyst component and o-diphenylphosphinobenzoic acid as the ligand catalyst component. The nickel salt was employed as an 8%w solution in 1,4-butanediol while the ligand was added as a 3.5%w solution in the diol solvent. The sodium borohydride and potassium hydroxide were added as a mixed aqueous solution, 9.4%w and 4.2%w, respectively.

The specific reaction conditions common to both the preformed catalyst case and the improvement according to the invention were as follows:

| | | |
|---|---|---|
| a. | Turnover time in reaction loop | 15 minutes |
| b. | Solvent/oligomer weight ratio | 10/1 |
| c. | Ethylene pressure in reaction loop | 1500 psig |
| d. | Oligomerization reaction temperature | 190–205° F. |
| e. | Weight ratio of recirculated reaction mixture to product drawn off reactor loop | 40:1 |
| f. | Mole ratio of nickel component to boron hydride component in catalyst or catalyst precursor | 0.5:1.0 to 0.7:1.0 |
| g. | Mole ratio of nickel component to base component in catalyst or catalyst precursor | 1.5:1.0 to 2.1:1.0 |
| h. | Concentration of ligand in reaction solvent | 90 to 100 wt. ppm |

Because of differences in the preparation of the catalyst in the preformed catalyst case versus the process of the invention there were some inherent differences in the two reaction systems. Further, certain reaction conditions were modified during the course of the continuous oligomerization according to the invention as compared to those employed in the preformed catalyst case in response to the improved properties of the catalyst prepared according to the invention. In particular, it was found that the quantity of nickel complex catalyst precursor could be substantially reduced relative to the quantity of ligand charged without any significant reduction in catalytic activity over that achieved with the preformed catalyst. These differences or modified reaction conditions are noted below with the reduced nickel complex consumption in the improvement according to the invention being expressed as a reduction in the mole ratio of nickel component to ligand component charged to the reaction zone:

| | |
|---|---|
| (1) Preformed catalyst case | |
| (a) temperature in catalyst preparation vessel | 100° F. |
| (b) ethylene pressure in catalyst preparation vessel | 1500 psig |
| (c) mole ratio of nickel component to ligand component in catalyst | 2.1:1.0 |
| (d) catalyst concentration in oligomerization reaction loop based on nickel input | 0.014% w. |
| (2) Improvement according to invention | |
| (a) temperature in catalyst precursor preparation vessel | 100°F. |
| (b) ethylene pressure in catalyst precursor preparation vessel | 1500 psig |
| (c) mole ratio of nickel component to ligand component in catalyst (range over test period) | 1.4:1.0 to 2.1:1.0 |
| (d) catalyst reaction loop based on nickel input (range over test period) | 0.009% w. to 0.014% w. |

The results of the continuous oligomerication reaction test program are recorded below in Table II. In this table, K factor is used in accordance with its definition given in the prior art e.g. see U.S. Pat. No. 4,020,121, to designate the distribution of oligomers by carbon number obtained in the oligomerization reaction product. This product distribution constant of K factor is a mathematical expression having the following definition:

$$K = \frac{\text{moles of } C_n + 2 \text{ Olefin}}{\text{moles of } C_n \text{ Olefin}} ; \quad (\text{for } n = 4, 6, 8 \ldots)$$

TABLE II

| Hours into Test Run | Mole Ratio of Nickel Component to Ligand Component | Approximate Rates of Oligomer Product Formation (lb/hr) | K factor |
|---|---|---|---|
| | Preformed catalyst case | | |
| 10 | 2.1 | 49,000 | 0.77–0.776 |
| | Improvement according to Invention | | |
| 11 | 2.1 | 52,500 | 0.783 |
| 13 | 2.1 | 53,200 | 0.788 |
| 15.5 | 1.75 | 56,700 | 0.788 |
| 20.5 | 1.65 | 55,300 | 0.776 |
| 32 | 1.65 | 53,200 | 0.778 |
| 34 | 1.40 | 56,000 | 0.754 |
| 60 | 1.40 | 53,200 | 0.750 |
| 75 | 1.40 | 50,400 | 0.754 |

Throughout the test run period using the process according to the invention the reaction loop remained consistently free of black or grey color which characterizes the presence of metallic nickel in the system. Further, as the test run according to the invention progressed, the reactor loop samples contained progressively less floc (presumably polymer) until at the end of the test the samples were essentially free of floc. The presence of black or grey color (metallic nickel) and floc in the reaction loop are inherent problems characterizing the use of the preformed catalyst of the prior art.

What is claimed is:

1. A process of oligomerizing ethylene to linear, alpha olefins which comprises reacting ethylene in an aliphatic diol solvent in an oligomerization reaction zone at elevated pressure with a nickel complex catalyst composition produced by combining in the reaction zone (a) a stable preformed complex of nickel, ethylene and hydride in an aliphatic diol solvent, said complex being prepared by contacting in the diol solvent and in the presence of ethylene (1) a simple divalent nickel salt (2) a base and (3) a boron hydride transfer agent and (b) a suitable bidentate ligand; the stable nickel complex in diol solvent and the bidentate ligand being added in separate portions to the reaction zone.

2. The process according to claim 1, wherein the bidentate ligand employed is an organo-phosphine having a tertiary organophosphorus moiety with a suitable functional group substituted on a carbon atom attached more than two carbon atoms from the phosphorus atom of the organophosphorus moiety.

3. The process according to claim 2, wherein the organophosphorus bidentate ligand is selected from compounds having the general formula:

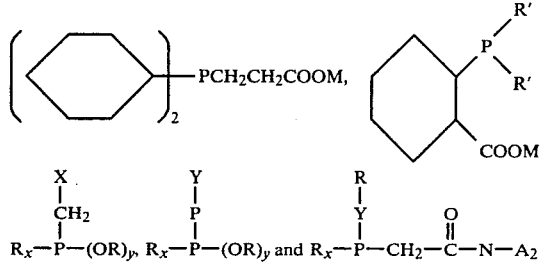

$$R_x-P-(OR)_y,\ R_x\overset{Y}{\underset{|}{-}}P-(OR)_y \text{ and } R_x-\overset{Y}{\underset{|}{P}}-CH_2-\overset{O}{\underset{||}{C}}-N-A_2$$

wherein R, independently, is a monovalent organo group, R' a monovalent hydrocarbyl group, X is carboxymethyl or carboxyethyl; Y is hydroxymethyl, mercaptomethyl, hydrocarbyl of up to 10 carbon atoms or hydrycarbyloxycarbonyl of up to 10 carbon atoms; A is hydrogen or an aromatic group of up to 10 carbon atoms; M is hydrogen or an alkali metal; x and y are zero, one or two and the sum of x and y is two, with the provison that when x is two the R groups may together with the phosphorus atom form a mono- or bicyclic heterocyclic phosphine having from 5 to 7 carbon atoms in each ring thereof.

4. The process according to claim 3, wherein the organophosphine bidentate ligand is an o-dihydricarbylphosphinobenzoic acid.

5. The process according to claim 3, wherein the organophosphine bidentate ligand is selected from the class consisting of o-diphenylphosphinobenzoic acid and dicyclohexylphosphinopropionic acid.

6. The process according to claim 3, wherein the simple divalent nickel salt has a solubility in the aliphatic diol solvent used to prepare the stable preformed complex of nickel, ethylene and hydride of at least 0.0005 mole per liter of solvent.

7. The process according to claim 6, wherein the simple divalent nickel salt is selected from the class consisting of nickel halides and nickel alkanoates; the base is selected from the class consisting of alkali metal hydroxdes and alkaline earth meatal hydroxides; the boron hydride transfer agent is selected from the class consisting of alkali metal borohydrides, alkali metal alkoxyborohydrides and tetraalkylammonium borohydrides and the aliphatic diol solvent employed to prepare the stable preformed complex of nickel, ethylene and hydride is an aliphtic diol of 2 to 7 carbon atoms selected from the class consisting of vicinal alkane diols and alpha, omega-alkane diols.

8. The process according to claim 7, wherein the stable preformed complex of nickel, ethylene and hydride in aliphatic diol solvent is prepared under an ethylene pressure of about 10 psig to about 5000 psig at a temperature of about 0° to about 100° C. and the oligomerization reaction as carried out under an ethylene pressure in the oligomerization reaction zone of about 10 to about 5000 psig at an oligomerization reaction zone temperature of about 50° to about 150° C.

9. The process according to claim 8, wherin the aliphatic diol solvent used to prepare the stable preformed complex solution of nickel, ethylene and hydride and the aliphatic diol solvent used in the oligomerization reaction zone are the same.

10. The process according to claim 9, wherein the stable preformed complex of nickel, ethylene and hydride is prepared using a nickel salt to boron hydride molor ratio of from about 0.2:1.0 to about 2.0:1.0 and a nickel salt to base molar ratio of about 0.33:1.0 to about 10.0:1.0 using sufficient aliphatic diol solvent to afford a nickel complex solution containing from about 0.002 to 0.2% by weight nickel.

11. The process according to claim 10, wherein the oligomerization reaction is carried out by adding the stable preformed complex of nickel, ethylene and hydride and the bidentate ligand to the oligomerization reaction zone at a molar ratio of nickel to ligand of from about 0.5:1.0 to about 5.0:1.0.

12. The process according to claim 11, wherein the preformed complex of nickel, ethylene and hydride in aliphatic diol solution and the bidentate ligand are added to the oligomerization reaction zone to provide a concentration of catalyst (calculated as parts per million of ligand in the diol reaction solvent) of at least 10 ppm.

13. The process according to claim 12, wherein the preparation of the stable preformed complex of nickel, ethylene and hydride in diol solvent and the oligomerization reaction are carried out continuously.

14. The process according to claim 13, wherein the amount of aliphatic diol solvent in the reaction zone ranges between about 0.1 to 1.0 liters of solvent per mole of ethylene.

15. The process according to claim 14, wherein the aliphatic diol solvent is 1,4-butanediol, the simple divalent nickel salt is nickel chloride, the boron hydride transfer agent is sodium borohydride, the base is potassium hydroxide and the bidentate ligand is o-diphenylphosphenobenzoic acid.

16. The process according to claim 15, wherein the oligomerization reaction is carried out by adding the stable preformed complex of nickel, ethylene and hydride in 1,4-butanediol and the bidentate ligand to the oligomerization reaction zone at a molar ratio of nickel to bidentate ligand of about 1.6:1.0.

* * * * *